United States Patent [19]

Fiato et al.

[11] Patent Number: 4,687,753

[45] Date of Patent: Aug. 18, 1987

[54] LASER PRODUCED IRON CARBIDE-BASED CATALYSTS

[75] Inventors: Rocco A. Fiato, Scotch Plains; Gary W. Rice, Whitehouse Station; Sabato Miseo; Stuart L. Soled, both of Pittstown, all of N.J.

[73] Assignee: Exxon Research and Engineering Company, Florham Park, N.J.

[21] Appl. No.: 791,509

[22] Filed: Oct. 25, 1985

[51] Int. Cl.[4] .................. B01J 37/34; B01J 27/22; B01J 19/12; C07C 1/04

[52] U.S. Cl. .................. 502/5; 204/157.41; 427/53.1; 502/177; 502/183; 502/184; 502/185; 518/714; 518/719; 518/721

[58] Field of Search ............... 502/5, 522, 177–179, 502/182–185; 423/439, 414; 427/53.1; 204/157.41

[56] References Cited

U.S. PATENT DOCUMENTS

| | | | |
|---|---|---|---|
| 2,486,894 | 11/1949 | Watson | 260/449.6 |
| 2,486,895 | 11/1949 | Watson | 260/449.6 |
| 2,535,042 | 12/1950 | Cohn et al. | 423/439 |
| 2,686,819 | 8/1954 | Johnson | 423/439 |
| 2,692,274 | 10/1954 | Kolbel et al. | 260/449.6 |
| 4,115,927 | 9/1978 | Rosensweig | 34/1 |
| 4,468,474 | 8/1984 | Gupta et al. | 502/5 |
| 4,518,707 | 5/1985 | Soled et al. | 502/177 |
| 4,537,867 | 8/1985 | Fiato et al. | 502/177 |
| 4,544,671 | 10/1985 | Soled et al. | 502/177 |
| 4,584,323 | 4/1986 | Soled et al. | 502/331 |

FOREIGN PATENT DOCUMENTS 0124901 11/1984 European Pat. Off. ....... 204/157.41

OTHER PUBLICATIONS

Barrault et al, React. Kinet. Catal. Lett., 17 (3–4), 373 (1981).
Solymosi et al, J. Chem. Soc., Faraday Trans., I 77, 1003 (1981).
Pijolat et al, CR. Acad. Sci., Paris, S. II, T295, pp. 343–346 (1982).
He et al, ACS Div. Petri. Chem., St. Louis, Apr. 1984, p. 332.
Weatherbee et al, J. Catalysis, 87, 352 (1984).
Gupta et al, SPIE, 458, Appl. of Lasers to Industrial Chemistry, 131–139 (1984).
Catal. Rev.—Sci. Engr., 21, 1980, p. 225 (Kobel Ralek).
Gilbert, A. G.; Sulzman, K. G. P.; J. Electrochem. Soc., 1974, 121, 832–834.

Primary Examiner—P. E. Konopka
Attorney, Agent, or Firm—E. Thomas Wheelock; Richard E. Nanfeldt

[57] ABSTRACT

This invention relates to a finely divided iron carbide-first row transition metal-based catalyst which is produced by a gas phase pyrolytic decomposition reaction driven by a laser. The catalysts may be used to produce various hydrocarbons, including olefins, from $CO_2$ and $H_2$.

32 Claims, 1 Drawing Figure

LASER SYNTHESIS REACTOR

LASER SYNTHESIS REACTOR

LASER PRODUCED IRON CARBIDE-BASED CATALYSTS

FIELD OF THE INVENTION

This invention relates to a finely divided iron carbide-based catalyst which is produced by a gas phase pyrolytic decomposition reaction driven by a laser. The catalysts may be used to produce various hydrocarbons, including olefins, from $CO_2$ and $H_2$.

BACKGROUND OF THE INVENTION

The increasing demand for energy has lead to renewed interest in non-traditional sources of feedstocks. For instance, coal was used as a source for gaseous fuel ("town gas") during earlier parts of this century. Much work was done at that time to produce higher molecular weight hydrocarbons from the synthesis gas. That work, involving the Fischer-Tropsch reaction based on $CO+H_2$ chemistry, was revived by Germany during World War II and currently enjoys moderate use at the SASOL plants in South Africa.

Research continues on the $CO-H_2$ chemistry because of the potential for converting low value feedstocks into higher value products.

Relatively little attention has been paid to the conversion of carbon dioxide into hydrocarbons. Carbon dioxide is the major product of combustion processes and is available at relatively high pressure as a diluent in many gas fields throughout the world.

The catalytic hydrogenation of $CO_2$ to produce hydrocarbons of various types is known. For instance, in Barrault et al, *React. Kinet. Catal. Lett.*, 17 (3–4) 373 (1981), a process for the production of hydrocarbons using iron-copper supported catalysts. Much of the hydrocarbon made is in the form of methane. Similarly, U.S. Pat. No. 2,692,274 (to Kolbel et al) shows the production of various hydrocarbons from $CO_2$ and $H_2$ using an apparently oxidic iron catalyst. Substantial methane appears to be produced.

In Solymosi et al, *J. Chem. Soc. Faraday Trans. I*, 77, 1003 (1981), the formation of methane from carbon dioxide using ruthenium on alumina is shown.

The disclosure in Pijolat et al, CR. Acad. Sci. Paris, S.II, T295, p. 343 (1982) deals with the hydrogenation of carbon dioxide over iron-on-alumina catalysts. The selectivity of the reaction to methane appears to be greater than 30%. Less than 40% of the $C_2$ to $C_4$ fraction is olefinic. See the Table on page 344.

In He et al, ACS Div. Petri. *Chem.*, St. Louis, April 1984, p. 332, a catalyst of $ZrO_2$ is shown to produce variously methane, methanol, branched alkanes and aromatics when fed $CO_2$ and/or CO.

A general study of the activities and selectivities of silica-supported Co, Fe and Ru in hydrogenating $CO_2$ is found in Weatherbee et al, *J. Catalysis*, 87, 352 (1984). The catalysts produced very high levels of $C_1$ and low levels of $C_2+$ products. The $C_2+$ olefin production was consequently low, although not specifically discussed.

The use of iron-containing catalysts to produce hydrocarbons from CO and $H_2$, in the presence of $CO_2$, has been shown in U.S. Pat. No. 2,486,894 and 2,486,895, both to Watson. There, $CO_2$ is used to minimize the production of $CO_2$.

None of the known prior art discloses the production of an iron carbide catalyst via laser pyrolysis for use in the production of hydrocarbons from $CO_2$ and $H_2$, much less in the production of olefinic products.

Others have described the use of iron-carbon containing catalysts produced by laser pyrolysis in Fischer-Tropsch reactions. The work of Gupta et al (in U.S. Pat. No. 4,468,474, issued Aug. 28, 1984 and in SPIE 458, Appl. of Lasers to Industrial Chemistry, 131–139 (1984)) shows the production of iron, carbon and silicon-containing catalysts by a laser and the catalysts' subsequent use in the Fischer-Tropsch process. Moderate activity and high $C_2-C_4$ olefin selectivity is asserted for the catalysts. Applicants' catalysts contain substantially no silicon.

No known prior art is believed to show the production of olefins from $CO_2$ and $H_2$ using the process and the catalyst described below.

SUMMARY OF THE INVENTION

The invention has several closely interrelated parts. The first deals with a process for pyrolyzing a volatile iron-carbon-containing-compound together with a volatile metal-carbon containing compound wherein the metal is a first row transition metal (preferably manganese, copper or zinc), optionally in the presence of an additional carbon containing compound, with a laser to produce a unique catalyst comprising iron, a first row transition metal, and carbon but substantially no silicon.

The fine particle iron-first row transition metal-carbon catalyst resulting from the laser pyrolysis step is considered to be an integral part of the invention.

Other variations of the invention involve processes using those catalysts and those disclosed in the parent applications in a reaction to produce hydrocarbons from $CO_2$ and $H_2$ generally and, specifically, to produce $C_2-C_4$ olefins.

DESCRIPTION OF THE PREFERRED EMBODIMENTS

Figure 1:
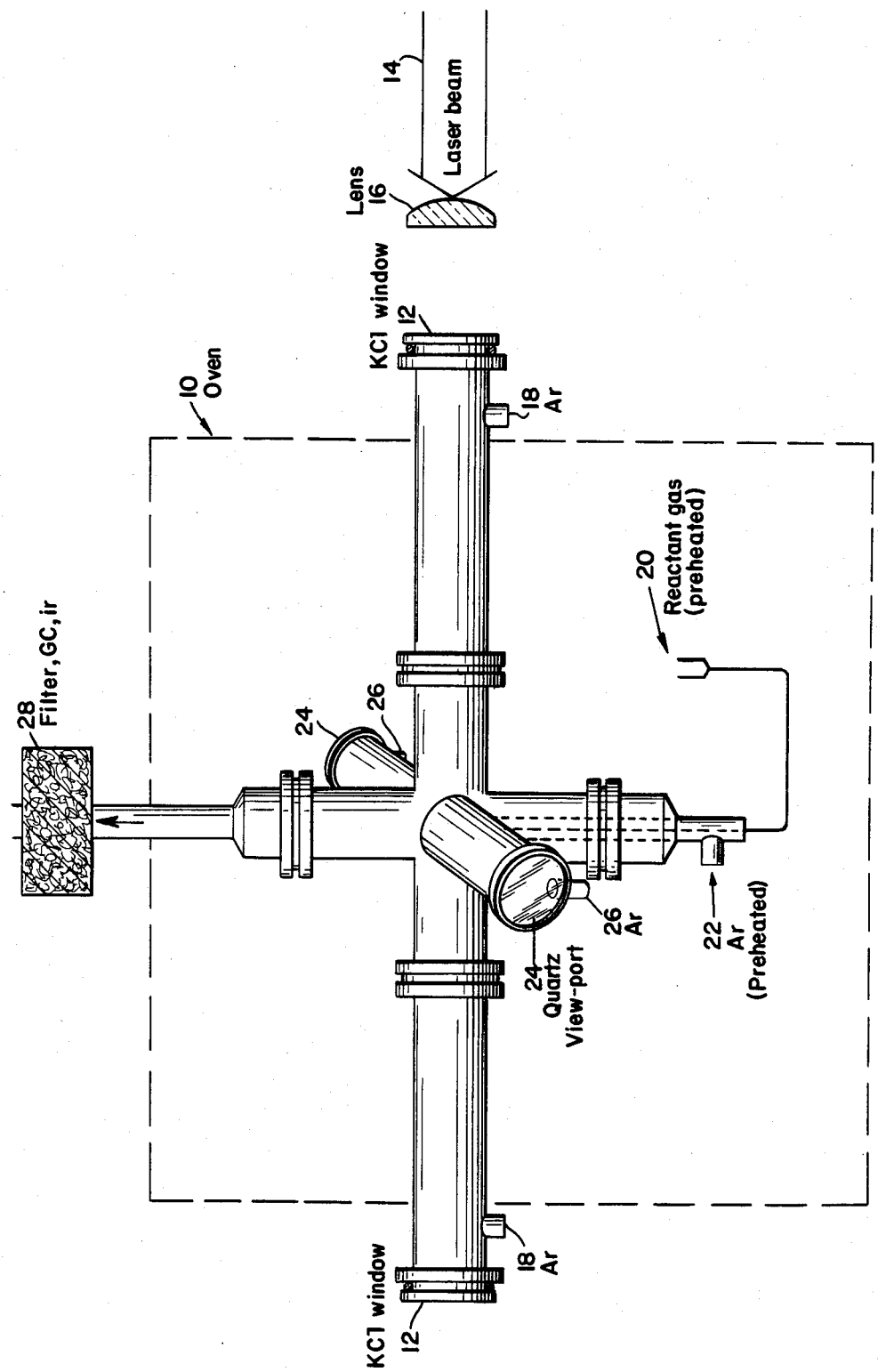

The present invention provides a finely divided catalyst composition comprising iron and carbon, at least a portion of which is an iron carbide, which is active for the conversion of $CO_2$ and $H_2$ into alkenes.

The catalyst composition of the instant invention may be prepared by gas phase pyrolytic decomposition of a mixture of a volatile organic iron-containing compound and a volatile organic first row transition metal containing compound (optionally in the presence of an additional carbon source) in the presence of a laser emission under conditions of laser power absorption, reactant and/or diluent flow rate and pressure to produce finely divided catalyst particles.

The organic-iron-containing compounds generally are iron carbonyls. Compounds such as $Fe(CO)_5$, ferrocene, and iron acetylacetonate are all suitable; $Fe(CO)_5$ is especially preferred. The term "first row transition metals" for the purpose of this invention includes Sc, Ti, V, Cr, Mn, Fe, Co, Ni, Cu and Zn. The first row transition metal containing materials may also be carbonyls, alkyls or alkyl carbonyls. Compounds such as $Mn_2(CO)_{10}$, $CH_3Mn(CO)_5$, $(OC)Cu(O^tBu)$, $(C_2H_5)_2Zn$ are examples of suitable cocatalyst precursors. The optional carbon source may act only as a diluent, depending upon reaction conditions, or may add a source of carbon to the pyrolysis reaction. The preferred carbon sources are short chain olefins such as ethylene. Obviously, at least one of the components must absorb the radiated laser energy.

The partial pressure of the metal-containing (both iron and first row transition metal) compounds depends upon the total pressure of the reactor but may be in the range of 20 to 500 torr; the optional carbon source may be 20 to 500 torr and a diluent such as argon or other noble gas may be included to bring the overall system pressure to a total of 200 to 1000 torr.

By "finely divided" catalyst particles is meant those having average diameters between 1 and 100 nm, preferably 10–50 nm. The materials usually have a BET surface area of 15 to 50 $m^2/gm$, preferably 20–35 $m^2/gm$. The catalyst has as at least a major portion, cementite, $Fe_3C$. The catalyst is a mixture of phases and, in addition to the cementite, may include $\alpha$ and $\gamma$ phase iron. The first row transition metal appears to be incorporated into the cementite lattice without substantial disruption of the lattice. The surface iron of the as-produced catalyst is carbidic iron. The $\alpha$ and $\gamma$-Fe phases appear to be embedded in the cementite. In some cases, the varying phases appear to be more than a simple physical mixture and may constitute a non-equilibrium mixture. A minimum amount of carbonaceous material is present on the exterior surface of the catalyst as a coating. The coating acts as a moderate passivating agent. No hydrogen pretreatment is needed to activate the as-prepared catalyst. The catalyst, as produced, is not pyrophoric. The catalyst may contain as much as about 10.0% oxygen but is substantially bereft of silicon. Although the method of producing this catalyst is believed to produce, of itself, a catalyst which is unique, the catalyst itself desirably contains no more than about 20% total carbon, preferably no more than about 12% total carbon and most desirably between 8% and 12% total carbon. It should be noted that the higher the percentage of excess matrix carbon, the generally lower the amount of $C_{10}$ olefins produced.

The laser used is preferably a continuous wave (cw) type capable of producing a flux of about 200 to 10,000 $W/cm^2$ in the reaction zone and further capable of resonant adsorption by a substance in the reaction zone. A $CO_2$ laser of adequate size is desirable. The residence time of the reactants in the laser beam should be between 1 and 60 ms. The quench rate for the products leaving the zone should be such that the total time the reactant/products are at the elevated temperature is 0.15 seconds or less. Quenching may be provided mainly by radiative energy loss from the reaction products.

It is to be understood that the reactor pressures and gas flow rates described herein are not critical to the synthesis of the catalyst, but are merely convenient for the particular reactor design employed. The only requirements are that the operating conditions be such that the time scale of the reaction be short enough to prevent deposition of excess carbon on the solid particles produced in the reaction, and that temperatures sufficient to drive the reaction be reached. Depending upon the power of the particular laser used to drive the reaction and the design of the particular reactor used to conduct the synthesis, a wide range of reactor pressures and gas flow rates will allow preparation of the catalyst.

By changing the reaction conditions, it is possible to obtain other products from the same reactants. For example, increasing the $Fe(CO)_5:C_2H_4$ ratio of 1:4 while maintaining the same laser power yields a product which is substantially all free iron and pyrophoric. Decreasing the residence time of the reactants in the laser beam has substantially the same effect. Similarly, increasing the laser power, or otherwise raising the reaction temperature, increases the carbon content of the product by continued decomposition of $C_2H_4$. An increase in reaction time would have a similar effect.

The catalyst particles may be used as-is; e.g., in an appropriate slurry reactor, or may be supported in one fashion or another as known in the art. The catalyst may be integrated with known supports to produce a larger catalyst matrix which may be handled with ease.

Promoters such as alkali metals, preferably potassium, or alkaline earth metals, such as magnesium, may be added using known methods. For instance, up to 10% potassium, preferably 2%, may be added to the as produced catalyst by impregnation with an aqueous solution of a potassium salt such as potassium carbonate. More difficultly soluble materials may be ground and mulled with the product Fe-C catalyst prior to a compaction step such as pilling, tabletting or extruding.

Of course, for certain applications, the catalytic material may be placed on a refractory support such as alumina, silica, mullite, diatomaceous earth, silica-alumina co-mixtures or other materials known to provide high surface area.

The process for conversion of $CO_2/H_2$ to the various hydrocarbon products may be practiced using the catalyst discussed above or using the catalysts disclosed in Ser. Nos. 735,768 and 735,769, to Fiato, Rice and Soled, filed May 20, 1985, the entirety of which are incorporated by reference. The process may be practiced as a fixed bed process or, preferably, as a slurry process. In the slurry process, the catalyst is suspended in a liquid hydrocarbon and the $CO_2/H_2$ mixture is forced through the catalyst slurry allowing good contact between the $CO_2/H_2$ and the catalyst to initiate and to maintain the hydrocarbon synthesis process. The slurry process is described in detail in such articles as Catal. Rev.-Sci. Engr., 21, 1980, pg, 225 (Kolbel, Ralek).

Advantages of a slurry process over that of a fixed bed process include better control of any exothermic heat of reaction produced during the reaction and better control over catalyst activity maintenance by allowing continuous recycle, recovery, and rejuvenation procedures to be implemented. The slurry process can be operated in a batch or in a continuous cycle, and in the continuous cycle, the entire slurry can be circulated in the system allowing for better control of the primary products' reaction zone residence time.

The slurry liquid used in the process is a liquid at the reaction temperature, should be chemically inert under the reaction conditions, should be a relatively good solvent for $CO_2/H_2$ and possess good slurrying and dispersing properties for the finely divided catalyst. Representative classes of organic liquids which can be utilized are high boiling paraffins, aromatic hydrocarbons, ethers, amines, or mixtures thereof. The high boiling paraffins include $C_{10}-C_{50}$ linear or branched paraffinic hydrocarbons; the aromatic hydrocarbons include $C_7-C_{20}$ single ring and multi- and fused ring aromatic hydrocarbons; the ethers include aromatic ethers and substituted aromatic ethers where the ether oxygen is sterically hindered from being hydrogenated; the amines include long chain amines which can be primary, secondary, and tertiary amines, wherein primary amines preferably contain at least a $C_{12}$ alkyl group in length, secondary amines preferably contain at least two alkyl groups being $C_7$ or greater in length, and tertiary amines preferably contain at least three alkyl groups being $C_6$ or higher in length. Representative examples of specific liquid slurry solvents useful are dodecane, tetradecane, hexadecane, octadecane, cosane, tetracosane, octacosane, dotriacontane, hexatritacosane, tetracontane, tetratetracontane, toluene, o-, m-, and p-xylene, mesitylene, $C_1$-$C_{12}$ mono- and multi-alkyl substituted benzenes, dodecylbenzene, naphthalene, anthracene, biphenyl, diphenylether, dodecylamine, di-nonylamine, trioctylamine, and the like. The preferred liquid hydrocarbon slurry solvent is octacosane or hexadecane.

The amount of catalyst used in the liquid hydrocarbon slurry solvent is generally about 10 to 60 g. of dry catalyst per 500 g. slurry liquid. Preferably about 30 to 50 g. dry catalyst per 500 g. slurry liquid slurry is utilized, being in about a respective 5:1 to 10:1 weight ratio.

The slurry system, comprised of the slurry liquid and finally divided catalyst, is generally stirred to promote good dispersion during the pretreatment in the process to avoid catalyst settling and to eliminate mass transport limitations between the gas and liquid phases.

The operating conditions for this process are generally as found below.

|  | Fixed Bed | Slurry |
|---|---|---|
| T °C. | 240–300 | 240–280 |
| (pref.) | 250–275 | 250–275 |
| Press. (psig) | 50–200 | 50–200 |
| (pref.) | 50–120 | 50–120 |
| $H_2/CO_2$ | 0.5–9:1 | 0.5–9:1 |
| (pref.) | 5–8:1 | 5–8:1 |
| SHSV (volume fresh gas/ volume catalyst/hr) | 100–10,000 | 100–10,000 |
| Stirrer speed (rpm) | — | 600–4000 |
| Recycle gases | $C_4^-$/$CH_4$/$CO_2$ | $C_4^-$/$CH_4$/$CO_2$ |
| Diluent gases | $N_2$/Ar/$CH_4$/ light hydrocarbons | $N_2$/Ar/$CH_4$/light hydrocarbons |

A magnetically stabilized fluidized bed as is described in U.S. Pat. No. 4,115,927 is also suitable for this reaction.

Generally speaking, higher temperatures tend to produce lighter products and more methane. Lower temperatures and higher pressures tend to lead to heavier hydrocarbons even in the wax range.

The feedstock is preferably made up of only $CO_2$ and $H_2$. Diluents such as noble gases (Ar, Ni, etc.), inert gases ($N_2$, etc.) or various volatile hydrocarbon gases ($CH_4$, $C_4^-$, etc) may be present if kept to acceptable minimums. Carbon monoxide may be present but should be kept to a very low value in that the catalyst appears to react first with CO to the general exclusion of $CO_2$. Little, if any, reaction of $CO_2$ takes place if the ratio of partial pressures $P_{CO_2}:P_{CO}$ is less than or equal to about 4:1. Again, with CO, the process is operable but not at an optimum $CO_2$ conversion rate.

The percent $CO_2$ conversion obtainable in the subject process, while providing substantial quantities of $C_2$-$C_{20}$ olefins, ranges from about 30 to 80 percent and usually about 50 to 60 percent for sufficient $C_2$-$C_{20}$ olefin production.

"Total hydrocarbons" produced in the process is related to the selectivity of percent $CO_2$ conversion to hydrocarbons and alcohols being those hydrocarbons from $C_1$ to about $C_{40}$ inclusive.

The percent $C_2$-$C_{20}$ hydrocarbons of the total hydrocarbons produced including methane and above is about 60 to 90 wt.%. The percent of $C_2$-$C_{20}$ olefins produced, of the $C_2$-$C_{20}$ total hydrocarbons produced is about 60 to 70 wt.%. A large portion of the olefins produced in the process are alpha olefins.

The selectivity to methane based on the amount of $CO_2$ conversion is about 1 to 10 weight percent of total hydrocarbons, produced. Preferably about 5 percent, and lower, methane is produced in the process.

Preferably, the reaction process variables are adjusted to minimize methane production, maximize percent $CO_2$ conversion, and maximize percent $C_2$-$C_{20}$ olefin selectivity, while achieving activity maintenance in the catalyst system.

Having thus described the invention, the following are examples which illustrate the various workings of it. They are not intended to limit the invention in any way.

EXAMPLE 1

The catalyst was prepared in a high surface area, low excess carbon form by a gas phase pyrolytic decomposition reaction driven by a cw $CO_2$ laser. The reactants were $Fe(CO)_5$ and $C_2H_4$. The $C_2H_4$ also served to absorb energy from the laser beam, allowing rapid heating of the reactants to reaction temperature. Post-reaction quenching is also very rapid, preventing extensive decomposition of the $C_2H_4$ on the catalyst particles and thus minimizing excess carbon content of the solid.

The reactor is shown in FIG. 1. It was constructed around a mini-flange 6-way cross. As shown in the Figure, the vertical axis of the apparatus was used for introduction of the reactants and take-off of products. One horizontal axis was used for passage of the laser beam, while the remaining horizontal axis was used for monitoring the reaction. Argon inlets were provided near each of the four windows to prevent deposition of particulates on the windows. The $C_2H_4/Fe(CO)_5$ mixture entered the cell through a tube which was concentric with a slightly larger tube to a point 1–4 mm below the laser beam. The outer tube was used to provide an argon stream surrounding the reactant stream, thereby promoting stable flow of the reactants into the laser beam.

The laser was operated in a cw mode on the 10 P(20) line at 944 cm$^{-1}$. Although not resonant with the 950 cm$^{-1}$ Q-branch of $C_2H_4$, this line is absorbed strongly enough by weaker $C_2H_4$ absorption bands to drive the pyrolytic reaction. The laser produced about 150 W in a beam focused to 6 mm diameter at the reaction zone, yielding a flux of 500 W/cm$^2$.

The synthesis was conducted at a reactor pressure of about 300 torr. The total argon flow to the four cell windows was about 700 SCCM (cc/min @ STP), while the argon flow coaxial to the reactants was also 70 SCCM. The $C_2H_4/Fe(CO)_5$ mixture was provided by bubbling $C_2H_4$ through liquid $Fe(CO)_5$ held at ambient temperature (23° C.) where the vapor pressure is 25 torr. [Gilbert, A. G.; Sulzmann, K. G. P., *J. Electrochem. Soc.* 1974, 121, 832–834.] The $C_2H_4$ flow rate was about 6 SCCM. Since the $Fe(CO)_5$ will essentially attain its equilibrium vapor pressure in the $C_2H_4$ stream under these flow conditions, the ratio of the reactants in the gas stream is determined by the total reactor pressure; $C_2H_4:Fe(CO)_5 = (300-25):25 = 11:1$.

The laser-driven reaction gave a bright yellow flame, indicating that quite high temperatures were obtained. Under the flow and pressure conditions given above, the residence time of the reactants in the laser beam is 25–40 ms and the quenching rate should be fast enough to keep the total time at high temperature, e.g., above about 500° C., to 0.1 s or less.

The solid products were collected on an 0.5 μm-pore Teflon membrane filter. The gaseous products were monitored by gas chromatograph (gc) and infrared detectors (ir). The ir showed that conversion of Fe(CO)$_5$ to products was quantitative under reaction conditions. The characteristic $\gamma$(CO) bands of Fe(CO)$_5$ could not be seen in the product gases, though free CO was present. The GC showed that most of the C$_2$H$_4$ did not react. The gas yields were to some extent dependent upon the linear flow rate of the reactant stream at the laser beam as shown below. Since the reactant stream does undergo some spreading as it enters the reactor, the linear velocity decreases with distance from the inlet tip. Raising the laser beam further above the inlet tip, or alternatively, decreasing the flow rate of the reactants, led to increased residence time of the reactants in the beam. The gas yields then indicated higher reaction temperature, or a longer reaction, or both, as demonstrated by the increase in yields of C$_2$H$_2$ and CH$_4$ relative to C$_2$H$_4$.

| Gas | Measured Mole %, TCD | |
|---|---|---|
| | High Flow | Low Flow |
| C$_2$H$_4$ | 64 | 57% |
| CO | 32 | 29% |
| C$_2$H$_2$ | 3.3 | 12.5% |
| CO$_2$ | 0.67 | 0.08% |
| CH$_4$ | 0.50 | 1.55% |

H$_2$ was also observed, but the peak area is not meaningful (He carrier). A peak for C$_2$H$_6$ could be observed by eye in the GC trace, but was so weak and broad that the integrator normally did not detect it. The yield was measured a 0.06% of the gases in one instance.

The analysis of one sample of solid prepared by the above method; was: Fe, 86.2% C, 12.74%; O, 1.73%; H, <035%. X-ray diffraction showed that the major phase present was Fe$_3$C or cementite. The BET surface area was 27 m$^2$/g, and XPS showed that the surface was carbon rich, with only Fe and C present. The catalyst so prepared was not pyrophoric and did not appear to oxidize significantly in air. Analysis by Mossbauer spectroscopy showed that Fe$_3$C was the major phase, with smaller amounts of $\alpha$-Fe and $\gamma$-Fe also present.

EXAMPLE II

Gas streams containing Fe(CO)$_5$/C$_2$H$_4$ were pyrolyzed using the method of Example I, with a cw CO$_2$ laser producing about 200 W, to yield powders containing Fe and C. The total pressure of the reactant gases was 385 torr. The partial pressure of Fe(CO)$_5$ and the flow rate of the C$_2$H$_4$ were varied. Analytical results for the powders are shown below.

| Synthesis | (a) | (b) | (c) | (d) |
|---|---|---|---|---|
| Fe(CO)$_5$ partial pressure, torr | 92 | 73 | 73 | 30 |
| C$_2$H$_4$ flow rate, ccm | 15 | 15 | 35 | 35 |
| Powder analysis, % Fe | 92.9 | 90.9 | 89.6 | 87.0 |
| Powder analysis, % C | 8.15 | 9.04 | 8.60 | 10.80 |
| Powder surface area, m$^2$/g | 20.4 | 22.2 | 24.1 | 34.8 |

All powders were shown to be mainly Fe$_3$C by X-ray diffraction.

These results demonstrate that the powder composition can be controlled by varying the preparation conditions.

EXAMPLE III

A laser generated Fe/Mn/C/O catalyst was made in a manner similar to that employed in Example I for the Fe/C catalyst, using Fe(CO)$_5$ and CH$_3$Mn(CO)$_5$ as the sources of the metals. The reactant gas mixture was prepared by bubbling one stream of C$_2$H$_4$ through liquid Fe(CO)$_5$ and passing a second C$_2$H$_4$ stream over solid CH$_3$Mn(CO)$_5$ and combining the two streams in a mixing tee. The resulting gas mixture was passed into the reactor shown in FIG. 1. The organometallic compounds were held at 53°–60° C. to obtain adequate vapor pressures. The Fe:Mn ratio in the product was controlled by independently varying the flow rates of C$_2$H$_4$ through the two organometallic reagent sources. Powders were obtained with BET surface areas of 24–31 m$^2$/g, and gave x-ray powder patterns characteristic of Fe$_3$C, indicating that the Mn was incorporated into the cementite lattice. Two typical preparations gave the following elemental analyses: (A) Fe, 71.3%; Mn, 16.3; C, 7.47; O, 7.54. (B) Fe, 69.9%, Mn, 15.2; C, 11.31; O, 3.51. The catalyst so obtained was not observed to be air sensitive.

EXAMPLE IV

A laser generated Fe/Zn/C catalyst was made in a manner similar to that employed in Example III, using Fe(CO)$_5$ and (C$_2$H$_5$)$_2$Zn as the first row transition metal source molecules. Separate streams of C$_2$H$_4$ were bubbled through the two liquid reactants, and the resulting streams were combined in a mixing tee and passed into the reactor shown in FIG. 1. The organometallic compounds were held at 40°–50° C. to obtain adequate vapor pressures. Powders were obtained with surface areas of 28–36 m$^2$/g, and gave x-ray powder patterns characteristic of Fe$_3$C. Two typical preparations gave the following elemental analyses: (A) Fe, 83.1%; Zn, 7.45; C, 9.23; O, 1.54. (B) Fe, 80.1%; Zn, 5.22; C, 13.23; O, 0.37. The catalyst so obtained was not air sensitive.

EXAMPLES V, VI, VII

Samples of the catalysts produced in Examples I, III and IV were separately placed in a continuous stirred tank reactor using octocosane to produce a slurry. A mixture of H$_2$, CO$_2$ and N$_2$ (as an internal standard) was introduced to the reactor. The results are tabulated below.

| Example No. | V | VI | VIII |
|---|---|---|---|
| Carbide Catalyst* | Fe | FeZn | Fe—Mn |
| % CO$_2$ Conversion | 22 | 25 | 31 |
| Selectivity (based on C$_1$$^+$) | | | |
| CH$_4$ | 5.5 | 5.8 | 5.1 |
| C$_2$$^+$ | 94.5 | 94.2 | 94.9 |
| % Olefins in C$_2$-C$_4$ | 94 | 93 | 96 |

Conditions: 270° C., 7/1 H$_2$/CO$_2$, 3800 v/g. Fe/hr, 75 psig, octacosane solvent, PARR CSTR, 26% vol. N$_2$ in feed as internal standard.
*Catalyst: laser generated iron carbide powders Fe—Mn and Fe—Zn materials contain 2% atom K promoter and <10% amorphous carbon in the catalyst matrix.

COMPARATIVE EXAMPLE VIII

The catalyst produced in Example I was compared in a continuously stirred slurry tank reactor to a conventional precipitated mixed metal Fe/Cu/K/Si catalyst produced by coprecipitation. The comparative oxide catalyst had a composition of 93/2/2/3 on a gram atom basis.

The results of the comparison are as follows:

| Catalyst | Example 1 Fe—C | Comparative Fe/Cu/K/Si |
|---|---|---|
| % $CO_2$ Conversion | 22 | 21 |
| Selectivity (based on $C_1^+$) | | |
| $CH_4$ | 5.5 | 64 |
| $C_2^+$ | 94.5 | 36 |
| % Olefin in $C_2$-$C_4$ | 94 | 28 |

Conditions: 260-270° C., 7/1 $H_2/CO_2$, 3800 v/g. Fe/hr, 75 psig, octacosane solvent, PARR CSTR, 26% vol. $N_2$ in feed as internal standard.

These results show the superior selectivity of the catalyst towards the production of olefins when compared to the known mixed metal oxide catalyst.

We claim as our invention:

1. A composition of matter comprising finely divided catalytic particles each particle containing iron, a transition metal, selected from the group consisting of Sc, Ti, V, Cr, Mn, Ni, Cu, and Zn, and carbon, in the substantial absence of silicon, at least a substantial portion of which particle is cementite, at least a substantial portion of said transition metal is in the cementite lattice, which particles are produced in a reaction zone in the presence of laser radiation under such conditions of laser flux density, power absorption, iron carbonyl reactant and transition metal compound reactant concentration and pressure to produce said particles having an average diameter of between 1 to 100 nm.

2. The composition of claim 1 wherein at least a portion of the iron is in the $\alpha$ and $\gamma$ phase.

3. The composition of claim 1 wherein the particles contain at least some free carbon.

4. The composition of claim 3 wherein at least some of said free carbon is situated on the particles' surface.

5. The composition of claim 1 wherein said average diameters are between 10 and 50 nm.

6. The composition of claim 1 wherein said iron reactant is $Fe(CO)_5$.

7. The composition of claim 1 additionally containing at least one promoter selected from alkali and alkaline earth metals which are added by impregnation from an aqueous salt solution.

8. The composition of claim 7 wherein said promoter is potassium.

9. The composition of claim 7 wherein said promoter is magnesium.

10. The composition of claim 1 wherein said particles are supported on a refractory matrix.

11. The composition of claim 7 wherein the particles are supported on a refractory matrix.

12. The composition of claim 1 wherein the first row transition metal is selected from manganese, copper, zinc, and nickel.

13. The composition of claim 1 wherein the first row transition metal is manganese.

14. The composition of claim 1 wherein the first row transition metal is copper.

15. The composition of claim 1 wherein the first row transition metal is zinc.

16. The composition of claim 7 wherein the first row transition metal is selected from the group of manganese, copper, nickel, and zinc.

17. The composition of claim 7 wherein the first row transition metal is manganese.

18. The composition of claim 7 wherein the first row transition metal is copper.

19. The composition of claim 7 wherein the first row transition metal is zinc.

20. A method for producing finely divided catalytic particles comprising the steps of:
introducing an iron carbonyl reactant and an organic first row transition metal compound selected from the group consisting of Sc, Ti, U, Cr, Mn, Ni, Cu and Zn into a reaction chamber into which a laser is focused at such conditions of total pressure, iron carbonyl and organic first row transition metal compound partial pressure, laser energy flux density and power absorption that finely divided particles at least a portion having a cementite structure comprising iron, a first row transition metal and carbon and having average diameters between 1 and 100 nm are produced.

21. The process of claim 20 wherein the iron carbonyl reactant is selected from the group consisting of and iron pentacarbonyl.

22. The process of claim 21 wherein the iron carbonyl reactant is iron pentacarbonyl.

23. The process of claim 22 wherein an additional hydrocarbon compound is introduced into said reaction chamber.

24. The process of claim 23 wherein the hydrocarbon compound is a low molecular weight alkene.

25. The process of claim 23 wherein the hydrocarbon compound is ethylene.

26. The process of claim 20 wherein the laser energy flux density in said reaction chamber is between 200 and 10,000 $W/cm^2$.

27. The process of claim 26 wherein the laser used to produce said laser energy flux density is a $CO_2$ laser operating in the continuous mode.

28. The process of claim 20 wherein the residence time of the reactants in the reaction zone is between 1 and 60 ms.

29. The process of claim 20 wherein the first row transition metal is selected from the group of manganese, copper, cobalt, nickel and zinc.

30. The process of claim 20 wherein the first row transition metal is manganese.

31. The process of claim 20 wherein the first row transition metal is copper.

32. The process of claim 20 wherein the first row transition metal is zinc.

* * * * *